United States Patent [19]

Aslam

[11] 4,101,279
[45] Jul. 18, 1978

[54] DEVICE FOR THE COLLECTION AND PROCESSING OF STOOL SPECIMENS

[76] Inventor: Muhammed Javed Aslam, 141 Linacre Rd., Winnipeg, Canada, R3T 3R5

[21] Appl. No.: 785,035

[22] Filed: Apr. 6, 1977

[51] Int. Cl.² ..................... B01L 3/00; G01N 33/16
[52] U.S. Cl. ........................................ 23/259; 4/1; 128/283; 366/314
[58] Field of Search ............... 23/259, 292; 73/421 R; 128/283; 4/1, 110; 259/8

[56] References Cited

U.S. PATENT DOCUMENTS

| 3,588,921 | 6/1971 | Nagel | 4/1 |
| 3,718,431 | 2/1973 | Wild | 128/283 X |
| 3,754,287 | 8/1973 | Taylor | 4/1 |
| 3,775,777 | 12/1973 | Roberts, Jr. | 4/110 X |
| 3,915,012 | 10/1975 | Fletcher et al. | 73/421 R |

FOREIGN PATENT DOCUMENTS 408,607   4/1934   United Kingdom ..................... 4/1

Primary Examiner—Morris O. Wolk
Assistant Examiner—Arnold Turk

[57] ABSTRACT

Disposable bowl is adapted to fit into a toilet bowl and to be supported thereby. It contains a blender blade assembly in the base thereof and a lid or cover is provided which can be secured to the container after same has been used. A connection extends into the bowl adjacent the upper side for injecting water or other fluid to wash down the sides of the bowl and also to dilute the stool specimen which may then be blended by engaging the device upon a conventional blender base. A further tube extends through the wall of the bowl for extraction of the necessary sample after blending whereupon the entire assembly may be disposed of without opening same.

17 Claims, 5 Drawing Figures

DEVICE FOR THE COLLECTION AND PROCESSING OF STOOL SPECIMENS

BACKGROUND OF THE INVENTION

This invention relates to new and useful improvements in devices for the collection and processing of human stool specimens.

The present method for the collection and processing of stool specimens from patients for laboratory analysis usually consists of giving the patient a bed pan or an open container. It is then left to the ingenuity of the patient to determine how to get the stool specimen into the container and after the specimen reaches the laboratory, the technician has to transport the sample to a mixing bowl or blender. The technician then blends the sample and obtains a representative sample for analysis.

This present system is quite offensive for the patient who may have to collect the sample for a 24 to a 72-hour period and it is also offensive for the technician.

The result is that the examination of stools, which can give valuable information for diagnosis, is often omitted or done in a half-hearted manner.

SUMMARY OF THE INVENTION

The present invention overcomes disadvantages inherent with present day methods of stool collection inasmuch as it is designed to make the collection of stool specimens much easier for the patient and their processing much less offensive for the technician.

One object of the invention is therefore to provide a device of the character herewithin described which consists of a disposable device for use with a conventional toilet bowl and seat therefor and with a source of power operating a blender blade assembly, for the collection and subsequent testing of formed stool samples; comprising in combination a bowl shaped open upper sided container, means to detachably support same upon the toilet bowl whereby the container is held in place by the seat of the toilet bowl, a separate cover for the fully open upper side of the container seatably engaged upon said upper side after the stool sample is in said container, means to introduce fluid into the container, a blender blade assembly within the base of said container and means to extract a sample of the stool speciment from the interior of said container after said sample has been blended by said blender blade assembly.

Another object of the invention is to provide a device of the character herewithin described which includes means for readily sealing the upper open end of the container once the specimen is in the container.

Another object of the invention is to provide a device of the character herewithin described which makes it much easier for the patient to collect the stool and to transmit same to the laboratory.

A yet further object of the invention is to provide a device of the character herewithin described in which the technician does not have to handle the specimen or remove it from the container inasmuch as the specimen is blended and the necessary sample readily extracted from the container which can then be thrown away still with the cover intact.

Yet another object of the invention is to provide a device of the character herewithin described which is simple in construction, economical in manufacture and otherwise well suited to the purpose for which it is designed.

With the foregoing objects in view, and other such objects and advantages as will become apparent to those skilled in the art to which this invention relates as this specification proceeds, my invention consists essentially in the arrangement and construction of parts all as hereinafter more particularly described, reference being had to the accompanying drawings in which:

DESCRIPTION OF THE DRAWINGS

In the drawings like characters of reference indicate corresponding parts in the different figures.

DETAILED DESCRIPTION

Proceeding therefore to describe the invention in detail, reference should be made to the drawings in which the device is collectively designated 10.

It consists of a container 11 having an open upper side 12, said container being manufactured from any desired material, but preferably synthetic plastic or cardboard.

Figure 1:
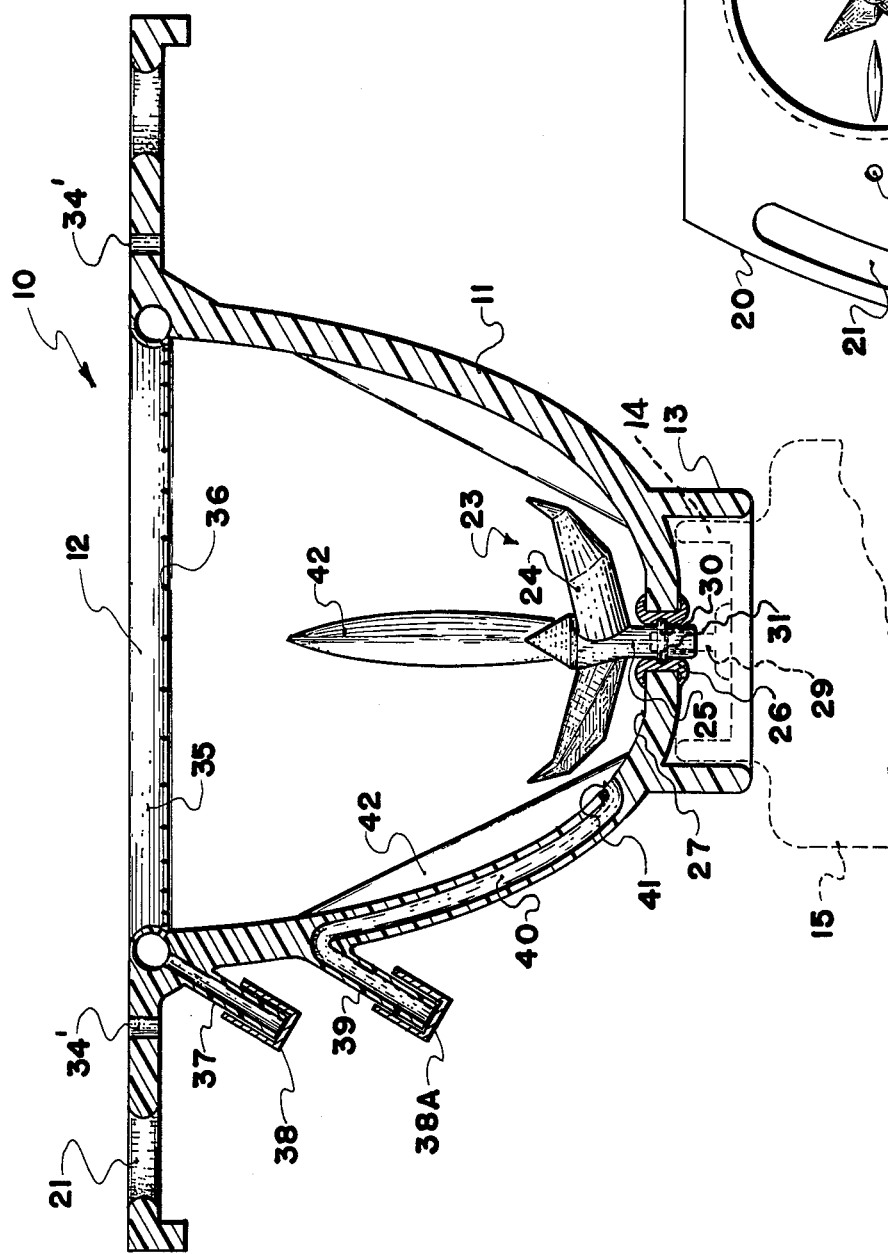
FIG. 1 is a cross sectional view of the invention with the cover removed.

The bowl-shaped container 11 is provided with a substantially circular base portion 13 which is adapted to fit over the upper end 14 of a conventional blender power unit 15, the upper portion of which is shown in dotted lines in FIG. 1.

Means are provided to support the container upon the rim 16 of a conventional toilet bowl assembly 17 which is provided with the conventional seat 18 hinged to the rear of the bowl as indicated by reference character 19.

Figure 5:
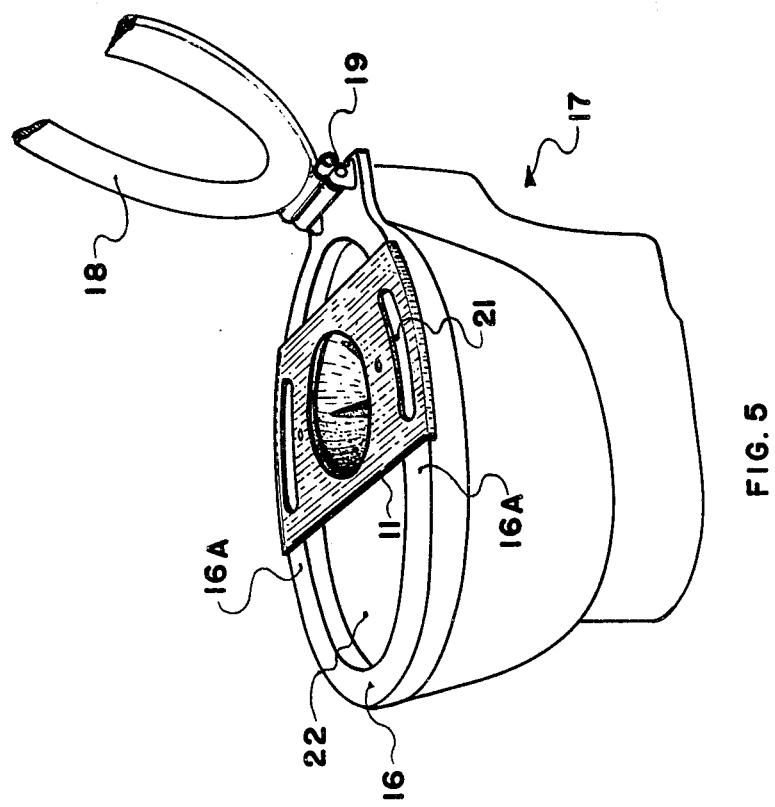
FIG. 5 is an isometric view of the device in place upon a toilet bowl.

The means to support the container comprise horizontally extending side flanges 20 formed in the same plane as the upper open side 12 and adapted to engage over the sides 16A of the rim 16 of the toilet bowl adjacent the rear thereof as clearly shown in FIG. 5, whereupon the seat 18 is folded downwardly upon the rim 16 thus holding the container firmly in position. Hand holds 21 are provided through the horizontal flanges 20 to facilitate the placement and removal of the container from the bowl 17.

It will be noted that when the container is in the position shown in FIG. 5, the front portion 22 of the bowl is left clear for urination so that the interior of the container is not contaminated.

A blender blade assembly collectively designated 23 is situated within the container in the base area thereof and includes a plurality of blender blades 24 mounted upon a spindle 25 journalled within a sleeve 26 which extends through the base portion 27 of the container and communicates with the interior of the base 13 as clearly shown.

The lower end of this spindle 25 is provided with a serrated recess 28 or the like adapted to engage over a correspondingly shaped blender spindle 29 extending upwardly from the portion 14 of the blender unit.

Means are provided to retain the spindle 25 and the blades 24 in position within sleeve 26 and one method is shown in FIG. 1 which comprises an annular bead 30 formed around the spindle 25 and snap engaging into a corresponding annular groove 31 within the sleeve 26.

However, other methods can be utilized. The blades 24 and the spindle 25 may be made from a synthetic plastic material as they are only used once and then discarded together with the container.

Figure 2:
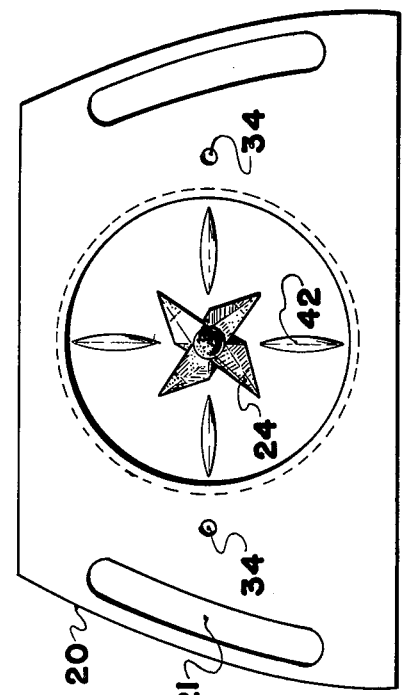
FIG. 2 is a top plan view of FIG. 1.
Figure 3:
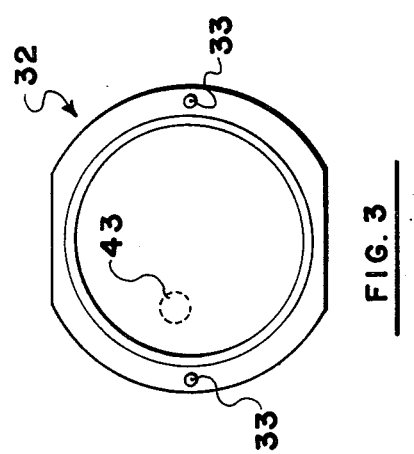
FIG. 3 is a plan view of the cover per se.
Figure 4:
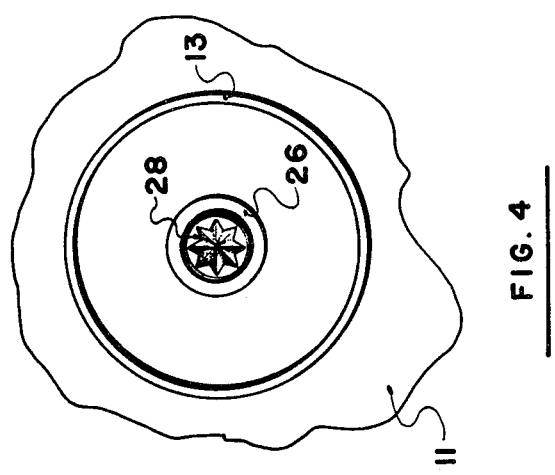
FIG. 4 is a fragmentary underside view of the container.

Means are provided to seal the upper open end 12 of the container after use, said means taking the form of a separate cover collectively designated 32 and shown in FIG. 3. This cover is shaped to cover the opened upper side 12 and to overlap upon the upper side of the container defining the open area thereof. Means are provided to assist in the locating of the cover comprising, in this embodiment, a pair of pins 33 extending from one side of the cover, adapted to engage corresponding apertures 34 formed in the upper side of the container between the open area 12 thereof and the hand holds 21 as clearly shown in FIG. 2. Means are also provided to engage the cover in sealing relationship with the container, and in this embodiment, the means comprise an annular band of pressure sensitive adhesive indicated by reference character 34' and normally covered, prior to use, with a protective strip (not illustrated) which is removed when it is desired to place the cover in position, other forms of sealing means may be provided.

Once sealed, the stool specimen is contained within the container and may be transmitted to the laboratory.

Means are provided to introduce water or other liquid into the container prior to blending to assist in the blending operation. In this embodiment, an annular tube is secured around the container adjacent the upper side 12 thereof, said tube being apertured as at 36 with the apertures directing inwardly to the inside of the container 11. A fluid inlet conduit 37 is operatively connected to this tube 35 and extends exteriorly of the container and the distal end is detachably covered by means of a flexible cap 38 until it is desired to introduce fluid into the container.

Once water or other fluid has been introduced through the conduit 37, the container is placed upon the blender as hereinbefore described and the contents are blended. In this regard, the formation of the tube 35 assists in washing down the sides of the container prior to the blending action.

Once blended, means are provided to extract a specimen from the container and in this connection, a discharge conduit 39 extends from the wall of the container and is covered by a cap 38A similar to cap 38. This conduit may be molded into the wall of the container as indicated by reference character 40 and extends downwardly towards the base area 27 and communicates with the interior of the container adjacent the base as indicated by reference character 41.

Once the specimen has been extracted, the entire assembly may be disposed of without detaching the cover 32 from the container.

It is desirable that a plurality of ribs 42 be formed on the inner surface of the walls of the container particularly adjacent the blender blade assembly 23 to facilitate the blending action.

It is also desirable to have a small circular area of weakness 43 formed in the cover in case the conduit 40 becomes blocked. This will permit the portion enclosed by the line of weakness to be punched out readily and easily and a tube inserted into the container for the extraction of the sample.

In summarizing, the patient simply lifts the toilet seat 18 and places the container in the back part of the bowl as indicated in FIG. 5, whereupon the seat is lowered into position. The patient may then use the toilet in the ordinary way, taking care that urine does not contaminate the stool sample in the container.

When the patient has finished, the adhesive strip (not illustrated) is peeled from the pressure sensitive adhesive area 34 on the lid 32 and the lid is positioned over the container with the pin 33 engaging the apertures 34, whereupon the lid may be pressed into position and sealed.

The container is then transmitted to the laboratory where the technician may weigh the container together with the specimen therein. By subtracting the known weight of the container, the technician is able to determine the exact weight of the specimen.

The container is then placed upon the blender base 15 and appropriate amounts of water or other liquid are added through the tube 35 to facilitate the blending. This also serves to clean the side of the container while blending.

After the blending action has been completed, a representative sample may be obtained through conduit 39 or by punching the aperture within the cover whereupon a tube may be passed downwardly into the container.

After the necessary samples have been taken, the entire assembly may be discarded without opening same.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What I claim as may invention is:

1. A disposable device for the collection and subsequent testing of formed stool samples, for use with a conventional toilet bowl and seat therefor and with a source of power operating a blender blade assembly; comprising in combination a bowl-shaped container having an open upper end and a base, means for detachably supporting said container upon a toilet bowl whereby the container is held in place by the seat of the toilet bowl, a separate cover for engaging the open upper end of the container in a sealing relationship after the stool sample is collected in said container, means to introduce fluid into the container when said cover is on said container, a blender blade assembly within the base of said container for blending the contents of said container when said cover is on said container, and means to extract a sample of the stool specimen from the interior of said container after said sample has been blended by said blender blade assembly and said cover is on said container.

2. The device according to claim 1 in which said means to extract a sample from said container includes a discharge conduit communicating through the wall of said container to adjacent the base thereof.

3. The device according to claim 1 in which said means to introduce fluid into said container includes a tube extending around said container adjacent the upper end thereof and communicating with the interior of said container, and a fluid inlet conduit outside of said container and being operatively connected to said tube.

4. The device according to claim 3 in which said means to extract a sample from said container includes a discharge conduit communicating through the wall of said container to adjacent the base thereof.

5. The device according to claim 1 in which said means to detachably support said container upon the toilet bowl includes horizontal flanges extending from opposite sides of said container for engaging the rim of a toilet bowl.

6. The device according to claim 5 in which said means to introduce fluid into said container includes a tube extending around said container adjacent the upper end thereof and communicating with the interior of said container, and a fluid inlet conduit outside of said container and being operatively connected to said tube.

7. The device according to claim 5 in which said means to extract a sample from said container includes a discharge conduit communicating through the wall of said container to adjacent the base thereof.

8. The device according to claim 1 which includes means for locating said cover upon said open upper end of said container.

9. The device according to claim 8 in which said means to introduce fluid into said container includes a tube extending around said container adjacent the upper end thereof and communicating with the interior of said container, and a fluid inlet conduit outside of said container and being operatively connected to said tube.

10. The device according to claim 8 in which said means to extract a sample from said container includes a discharge conduit communicating through the wall of said container to adjacent the base thereof.

11. The device according to claim 8 in which said means to detachably support said container upon the toilet bowl includes horizontal flanges extending from opposite sides of said container for engaging the rim of a toilet bowl.

12. The device according to claim 11 in which said means to introduce fluid into said container includes a tube extending around said container adjacent the upper end thereof and communicating with the interior of said container, and a fluid inlet conduit outside of said container and being operatively connected to said tube.

13. The device according to claim 8 in which said cover is substantially planar, said container including a wall defining said open upper end thereof, said means for locating said cover including pins projecting downwardly from said cover engageable within apertures formed in said wall of said container defining said upper open end thereof.

14. The device according to claim 13 in which said means to introduce fluid into said container includes a tube extending around said container adjacent the upper end thereof and communicating with the interior of said container, and a fluid inlet conduit outside of said container and being operatively connected to said tube.

15. The device according to claim 13 in which said means to extract a sample from said container includes a discharge conduit communicating through the wall of said container to adjacent the base thereof.

16. The device according to claim 13 in which said means to detachably support said container upon the toilet bowl includes horizontal flanges extending from opposite sides of said container for engaging the rim of a toilet bowl.

17. The device according to claim 16 in which said means to introduce fluid into said container includes a tube extending around said container adjacent the upper end thereof and communicating with the interior of said container, and a fluid inlet conduit outside of said container and being operatively connected to said tube.

* * * * *